US00PP20116P3

(12) United States Plant Patent
Layt

(10) Patent No.: US PP20,116 P3
(45) Date of Patent: Jun. 23, 2009

(54) ***LIRIOPE MUSCARI* PLANT NAMED 'LIRJ'**

(50) Latin Name: *Liriope muscari*
Varietal Denomination: LIRJ

(76) Inventor: Todd Anthony Layt, P.O. Box 1011, Richmond, NSW (AU), 2753

( * ) Notice: Subject to any disclaimer, the term of this patent is extended or adjusted under 35 U.S.C. 154(b) by 0 days.

(21) Appl. No.: 12/077,555

(22) Filed: Mar. 20, 2008

(65) Prior Publication Data

US 2008/0235840 P1 Sep. 25, 2008

Related U.S. Application Data

(60) Provisional application No. 60/919,799, filed on Mar. 23, 2007.

(51) Int. Cl.
*A01H 5/00* (2006.01)

(52) U.S. Cl. ..... Plt./450
(58) Field of Classification Search ..... Plt./450
See application file for complete search history.

*Primary Examiner*—Annette H Para

(57) ABSTRACT

'LIRJ' is a distinctive variety of *Liriope muscari* which is characterized by the combination of medium-tall plant height combined with narrow-medium leaf width, broad leaf thickness, dense foliage and a purple violet flower color.

1 Drawing Sheet

Latin name of the genus and species: The Latin name of the genus and species of the novel variety disclosed herein is *Liriope muscari.*

Variety denomination: The inventive variety of *Liriope* disclosed herein has been given the variety denomination 'LIRJ'.

BACKGROUND OF THE INVENTION

The present invention relates to a new and distinct perennial variety of *Liriope muscari,* which has been the variety denomination of 'LIRJ'. Its market class is that of an ornamental plant 'LIRJ' is intended for use in landscaping and as a decorative plant.

The *Liriope muscari* variety 'LIRJ' was finally selected in 2002 in an Australian nursery in the state of New South Wales following a selection process carried out from 1999 to 2002 involving approximately 30000 seedlings of *Liriope muscari.* 'LIRJ' is a seeding selection from open pollinated *Liriope muscari.* 'LIRJ' was selected due to its medium-tall plant height combined with narrow-medium leaf width and dense foliage. 'LIRJ' was first propagated asexually by division in the state of New South Wales, Australia and has since between asexually propagated by division and micropropagation. The distinctive characteristics of the inventive 'LIRJ' variety are stable from generation to generation, clones of the variety produced by asexual reproduction maintain the distinguishing characteristics of the original plant.

'LIRJ' has an upright growth habit with a very strong shoot density whereas *Liriope muscari* has an upright to semi upright growth habit, tending to spread more, with a medium shoot density. 'LIRJ' has a tall plant height whereas *Liriope muscari* has a medium plant height (40–50 cm). 'LIRJ' has a narrow-medium leaf width whereas *Liriope muscari* has a board leaf width. 'LIRJ' has a thick leaf width whereas *Liriope muscari* has a medium leaf thickness.

An application for plant breeders' rights for variety 'LIRJ' has been lodged with the Australian Plant Breeders' Rights Office, and was first gazetted in 27 Mar. 2006 under Application No. 2006/037.

SUMMARY OF THE INVENTION

'LIRJ' is a distinctive variety of *Liriope muscari* which is characterized by the combination of its medium-tall plant height combined with narrow-medium leaf width, broad leaf thickness, dense foliage and a purple violet flower color.

BRIEF DESCRIPTION OF THE FIGURES

FIG. 2 shows an inflorescence of an 'LIRJ' plant showing flower detail.

BOTANICAL DESCRIPTION OF THE PLANT

Figure 1:
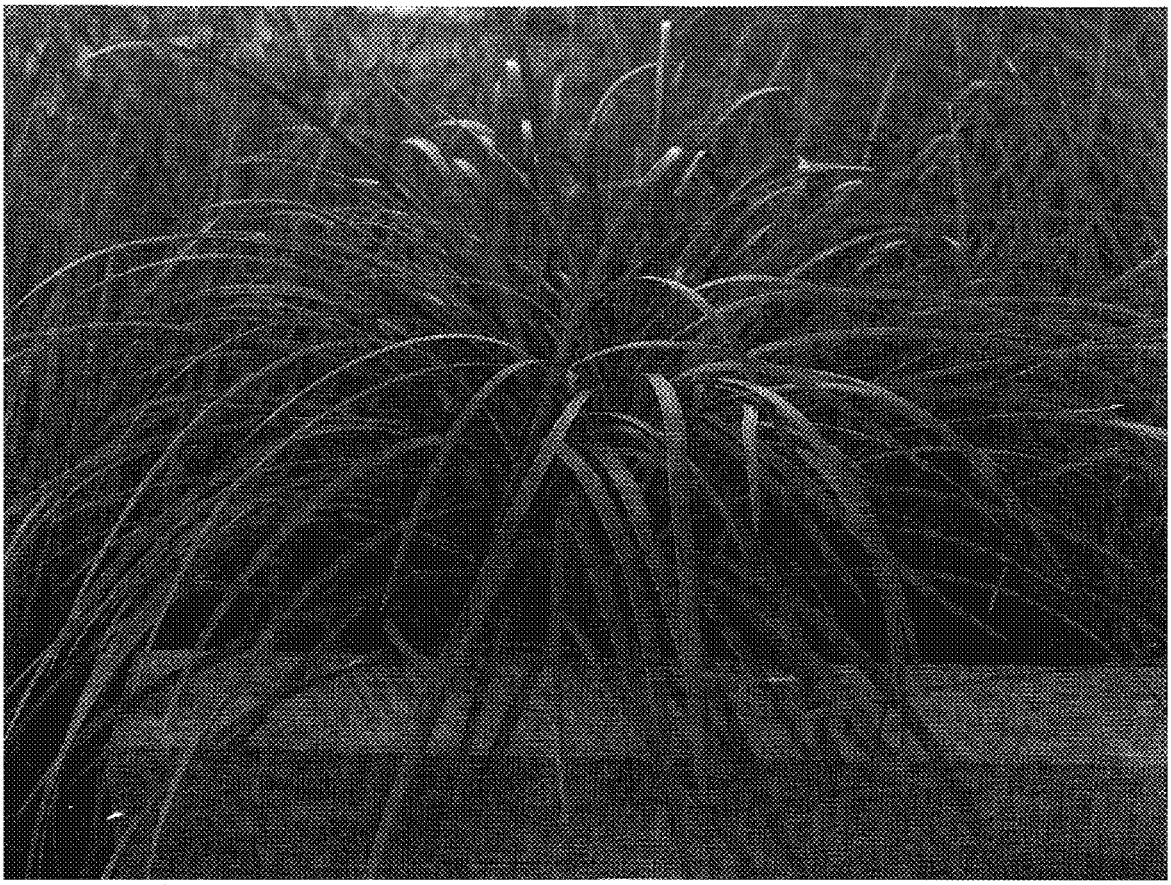
FIG. 1 shows a 'LIRJ' plant.

The following is a detailed botanical description of a new and distinct variety of a *Liriope muscari* ornamental plant known as 'LIRJ'. Plant observations were made on plants grown in New South Wales, Australia. Unless indicated otherwise, the descriptions disclosed herein are based upon observations made in February 2006 of mature 'LIRJ', 24 months old, plants grown in nursery pots.

Those skilled in the art will appreciate that certain characteristics will vary with older or, conversely, younger plants, 'LIRJ' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart,* The Royal Horticultural Society, London, 1995 edition. Note that generic color descriptions such as 'pink' do not exist in the R.H.S. charts and the corresponding R.H.S. colors are quoted.

'LIRJ' is a perennial *Liriope muscari* plant which is a seedling selection from *Liriope muscari.* After its selection, 'LIRJ' was asexually propagated by division and then by micropropagation. 'LIRJ' has a green leaf color and purple flowers displayed within the foliage.

These features and other characteristics are apparent from the description provided below.

Growth Habit, Dimensions and Color

'LIRJ' is a medium-tall plant forming an upright clump with slightly spreading leaves and arching and weeping leaves as the foliage matures. Average plant height is to 60–65 cm and average plant spread is to 90–95 cm in a mature plant grown in a garden in Sydney, New South Wales, Australia (observed January 2007). A representative 'LIRJ' plant is shown in FIG. 1. The upper side of the mature leaf is yellow green in color (observed January 2007) corresponding to approximately RHS 147A.

Leaf margins and mid ribs to not contrast prominently with the leaf blade. The leaf lower side color corresponds to the upper leaf side but has a less glossy surface texture. The leaf is generally 6–7 mm in width, and reaches an average length of 40–50 cm. The leaf shape is ligulate-ensiform, leaf base is cauline, leaf margin is entire, leaf apex is acute and leaf surface texture is glossy and glabrous. The leaf venation pattern is parallel; the color is the same as the rest of the leaf. The leaf attitude is erect to semi erect with arching and weeping of foliage at maturity.

Roots

The roots of 'LIRJ' are colored white and fleshy and thick, similar to other *Liriope muscari.*

Inflorescence

The inflorescence is a raceme with flowers borne in clusters of typically 3. Each flower cluster consists of pedicellate flowers ranging from a very short pedicel length (almost sessile) to up to 5 mm long. Inflorescence length is approximately 20–24 cm on average and the raceme position is within the foliage at anthesis. Raceme length is 11–13 cm on average. Peduncle color is grayed purple RHS 183A-B mixed with yellow green approximately RHS 146C-D creating an overall purple appearance. Each flower cluster is subtended by a small bract colored yellow green approximately RHS 146C. Pedicel color is initially white RHS155C changing to purple violet RHS 82D as the flower opens. The flowering season in Sydney, NSW, Australia is early December until Late February.

Flowers

Flower bud color is yellow RHS 11D (immature) and purple violet RHS 82C-D just prior to opening. Mature petal color is purple violet RHS 82B. Anthers are yellow RHS 6B. Flower diameter is approximately 4–5 mm when fully opened.

Comparison of LIRF with Other Varieties of *Liriope muscari*

'LIRJ' differs from the variety 'Evergreen Giant' (unpatented) as it has a narrow-medium leaf width, very dense foliage and lighter purple violet colored flowers whereas 'Evergreen Giant' has a medium leaf width (8–10 mm), a weak density foliage and lighter looking purple violet colored flowers corresponding to RHS 82D. 'LIRJ' has a plant height of 60–65 cm whereas 'Evergreen Giant' has a plant height of 70–75 cm. 'LIRJ' has a broad leaf thickness creating a strong leaf whereas 'Evergreen Giant' has a medium leaf thickness. 'LIRJ' has flowers borne in clusters of 3 along the whole peduncle whereas 'Evergreen Giant' has flowers borne in clusters of 4 towards the base changing to clusters of 3 towards the apex.

'LIRJ' differs from the variety 'Big Blue' (unpatented) as it has a narrow-medium leaf width, very dense foliage and lighter purple violet colored flowers whereas 'Big Blue' has a broad leaf width (11–12 mm) and medium density foliage and darker looking violet colored flowers corresponding to RHS 86B.

'LIRJ' differs from the variety 'Bigun' (U.S. Plant Pat. No. 15,474), narrow-medium leaf width, an absence of leaf twisting and purple violet colored flowers whereas 'Bigun' has a medium plant height (to 60 cm), broad leaf width (to 18 mm), leaf twisting present and flower color corresponding to violet blue RHS 92A.

'LIRJ' differs from the variety 'Royal Purple' (unpatented) as it has a narrow-medium leaf width, strong shoot density, short inflorescence height with flowers displaying within the foliage whereas 'Royal Purple' has a broad leaf width, weak shoot density, medium inflorescence height with flowers displaying slightly above the foliage.

The combination of its medium-tall plant height combined with narrow-medium leaf width, broad leaf thickness, dense foliage and a purple flower color makes 'LIRJ' a desirable ornamental plant suited for mass production for pot and landscape use.

Asexual Reproduction

After its initial discovery, 'LIRJ' was transplanted into a 140 mm pot for further trials and testing. After divisions were made for several subsequent generations. 'LIRJ' was observed to retain color and size characteristics that were noted in the original 'LIRJ' seedling. Divisions of 'LIRJ' root within 2 to 3 weeks. 'LIRJ' was divided into several pots for further evaluation. Potting mix used contained 50% sand and 50% peat. Plants were divided into 90 mm×50 mm×50 mm tubes.

'LIRJ' has been propagated in vitro using micropropagation and has been observed to reproduce from generation to generation in a uniform and stable manner maintaining original color and size characteristics.

Environmental Tolerances

'LIRJ' has typical shade tolerance for the species. The winter hardiness of 'LIRJ' is at least to zone 8a–8b in the Southeastern United States, and evaluation of winter hardiness is ongoing. 'LIRJ' has moderate to good drought tolerance. 'LIRJ' has moderate to good recovery with watering after severe wilting. 'LIRJ' does well in sandy soils, but also tolerates heavy, clay-type soils well.

Disease Resistance

'LIRJ' has typical resistance to fungal and bacterial pathogens compared to other similar *Liriope muscari* cultivars.

That which is claimed is:

1. A new and distinct variety of *Liriope muscari* plant named 'LIRJ' substantially as described and illustrated herein.

* * * * *